United States Patent
Watanabe et al.

(10) Patent No.: US 6,642,401 B2
(45) Date of Patent: Nov. 4, 2003

(54) β-DIKETONATOCOPPER(I) COMPLEX CONTAINING ALLENE COMPOUNDS AS LIGAND AND PROCESS FOR PRODUCING THE SAME

(75) Inventors: Hisayuki Watanabe, Funabashi (JP); Hideki Musashi, Funabashi (JP); Yasuo Kawamura, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/203,274

(22) PCT Filed: Mar. 13, 2001

(86) PCT No.: PCT/JP01/01956
§ 371 (c)(1),
(2), (4) Date: Aug. 8, 2002

(87) PCT Pub. No.: WO01/68580
PCT Pub. Date: Sep. 20, 2001

(65) Prior Publication Data
US 2003/0109734 A1 Jun. 12, 2003

(30) Foreign Application Priority Data
Mar. 14, 2000 (JP) .......................... 2000-069814

(51) Int. Cl.[7] .............. C07F 1/08; C23C 16/00
(52) U.S. Cl. ............ 556/12; 556/41; 556/112; 556/117; 427/593
(58) Field of Search ............ 556/12, 41, 112, 556/117; 427/593

(56) References Cited

U.S. PATENT DOCUMENTS

| 4,425,281 A | * | 1/1984 | Doyle | 556/41 |
| 6,534,666 B1 | * | 3/2003 | Zorich et al. | 556/41 |

FOREIGN PATENT DOCUMENTS

| EP | 0 493 754 A1 | 7/1992 |
| EP | 0 498 269 A2 | 8/1992 |
| EP | 0 533 070 A2 | 3/1993 |
| JP | A 5-59551 | 3/1993 |

* cited by examiner

*Primary Examiner*—Porfirio Nazario-Gonzalez
(74) *Attorney, Agent, or Firm*—Oliff & Berridge, PLC

(57) ABSTRACT

A β-diketonatocopper(I) complex which contains as a ligand (L) an allene compound and is represented by formula (2)

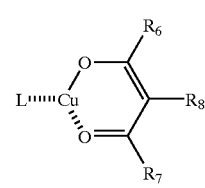

(2)

wherein, $R_6$ and $R_7$ may be the same or different and each represents linear or branched $C_{1-4}$ alkyl, $C_{1-4}$ alkoxy, or linear or branched $C_{1-4}$ fluoroalkyl, $R_8$ represents hydrogen or fluorine, and L represents the allene compound, and a process for producing the same. The complex is useful in forming a thin copper film by metal-organic vapor deposition (hereinafter abbreviated as MOCVD) method.

2 Claims, No Drawings

β-DIKETONATOCOPPER(I) COMPLEX CONTAINING ALLENE COMPOUNDS AS LIGAND AND PROCESS FOR PRODUCING THE SAME

TECHNICAL FIELD

The present invention relates to a β-diketonatocopper(I) complex useful in forming a thin copper film by metal-organic vapor deposition (hereinafter abbreviated as MOCVD) method and a process for producing the same.

BACKGROUND ART

Conventionally, as a raw material for forming a thin copper film by MOCVD method, is well known β-diketonatocopper(I) complex comprising (vinyltrimethylsilane) (1,1,1,5,5,5-hexafluoro-2,4-pentanedionato) copper(I) of formula (α)

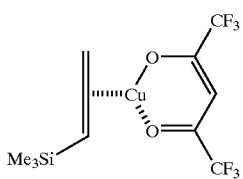

(α)

disclosed in Japanese Patent Laid-open No. Hei 5-59551.

However, vinyltrimethylsilane is used as a ligand for the β-diketonatocopper(I) complex of the formula (α). Conventionally, β-diketonatocopper(I) complex in which an allene compound is used as a ligand has not been known.

DISCLOSURE OF INVENTION

The present inventors research hard to find out novel β-diketonatocopper(I) complex in which an allene compound is used as a ligand from the above-mentioned viewpoint, and come to obtain β-diketonatocopper(I) complexes of formula (2) described below in which an allene compound of formula (1) described below is used as a ligand.

That is, the present invention relates to a β-diketonatocopper(I) complex which contains as a ligand (L) an allene compound of formula (1)

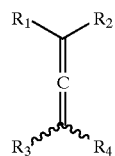

(1)

wherein $R_1$, $R_2$, $R_3$ and $R_4$ may be the same or different and each represents hydrogen, $C_{1-4}$ alkyl or $(R_5)_3Si-$, or $R_1$ and $R_2$, together with the carbon atom bonding them, may form 3- to 6-member ring, or $R_2$ and $R_3$, together with the allene bond group bonding them, may form 8- to 10-member ring, $R_5$s may be the same or different and independently of one another represent linear or branched $C_{1-4}$ alkyl, and which is represented by formula (2)

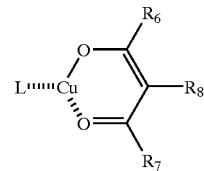

(2)

wherein, $R_6$ and $R_7$ may be the same or different and each represents linear or branched $C_{1-4}$ alkyl, $C_{1-4}$ alkoxy, or linear or branched $C_{1-4}$ fluoroalkyl, $R_8$ represents hydrogen or fluorine, and L represents the allene compound of formula (1).

Then, the present invention will be concretely explained.

The following is exemplified for each of the substituents in the chemical structural formula of allene compounds represented by formula (1) that is the ligand in the β-diketonatocopper(I) complexes of formula (2).

The substituents $R_1$, $R_2$, $R_3$ and $R_4$ include, for example H, Me, Et, n-Pr, n-Bu, i-Pr, i-Bu, s-Bu, t-Bu, Me$_3$Si, Et$_3$Si, n-Pr$_3$Si, n-Bu$_3$Si, i-Pr$_3$Si, i-Bu$_3$Si, s-Bu$_3$Si, t-Bu$_3$Si, Me$_2$(Et)Si, Me$_2$(n-Pr)Si, Me$_2$(n-Bu)Si, Me$_2$(i-Pr)Si, Me$_2$(i-Bu)Si, Me$_2$(s-Bu)Si, Me$_2$(t-Bu)Si, Et$_2$(Me)Si, Et$_2$(n-Pr)Si, Et$_2$(n-Bu)Si, Et$_2$(i-Pr)Si, Et$_2$(i-Bu)Si, Et$_2$(s-Bu)Si, Et$_2$(t-Bu)Si, n-Pr$_2$(Me)Si, n-Pr$_2$(Et)Si, n-Pr$_2$(i-Pr)Si, n-Pr$_2$(n-Bu)Si, n-Pr$_2$(s-Bu)Si, n-Pr$_2$(t-Bu)Si, n-Bu$_2$(Me)Si, n-Bu$_2$(Et)Si, n-Bu$_2$(n-Pr)Si, n-Bu$_2$(i-Pr)Si, n-Bu$_2$(i-Bu)Si, n-Bu$_2$(s-Bu)Si, n-Bu$_2$(t-Bu)Si, i-Pr$_2$(Me)Si, i-Pr$_2$(Et)Si, i-Pr$_2$(n-Pr)Si, i-Pr$_2$(n-Bu)Si, i-Pr$_2$(s-Bu)Si, i-Pr$_2$(t-Bu)Si, i-Bu$_2$(Me)Si, i-Bu$_2$(Et)Si, i-Bu$_2$(n-Pr)Si, i-Bu$_2$(n-Bu)Si, i-Bu$_2$(i-Pr)Si, i-Bu$_2$(s-Bu)Si, i-Bu$_2$(t-Bu)Si, s-Bu$_2$(Me)Si, s-Bu$_2$(Et)Si, s-Bu$_2$(n-Pr)Si, s-Bu$_2$(n-Bu)Si, s-Bu$_2$(i-Pr)Si, s-Bu$_2$(i-Bu)Si, s-Bu$_2$(t-Bu)Si, t-Bu$_2$(Me)Si, t-Bu$_2$(Et)Si, t-Bu$_2$(n-Pr)Si, t-Bu$_2$(n-Bu)Si, t-Bu$_2$(i-Pr)Si, t-Bu$_2$(i-Bu)Si or t-Bu$_2$(s-Bu)Si.

When $R_1$ and $R_2$, together with the carbon atom bonding them, form 3- to 6-member ring, the ring includes cyclopropane ring, cyclobutane ring, cyclopentane ring or cyclohexane ring.

When $R_2$ and $R_3$, together with the allene bond group bonding them, form 8- to 10-member ring, the ring includes cyclooctane ring, cyclononane ring or cyclodecane ring.

The following is exemplified for each of the substituents in the chemical structural formula of the β-diketonatocopper (I) complexes of formula (2).

The substituents $R_6$ and $R_7$ include, for example, CF$_3$, C$_2$F$_5$, n-C$_3$F$_7$, i-C$_3$F$_7$, n-C$_4$F$_9$, Me, Et, n-Pr, n-Bu, i-Pr, i-Bu, s-Bu, t-Bu, MeO, EtO, n-PrO, n-BuO, i-PrO, i-BuO, s-BuO or t-BuO. In addition, the substituent $R_8$ includes, for example H or F.

The present invention also relates to a process for producing a β-diketonatocopper(I) complex represented by formula (2)

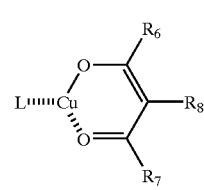

(2)

wherein, $R_6$ and $R_7$ may be the same or different and each represents linear or branched $C_{1-4}$ alkyl, $C_{1-4}$ alkoxy, or linear or branched $C_{1-4}$ fluoroalkyl, $R_8$ represents hydrogen or fluorine, and L represents the allene compound of formula (1), characterized in that the process comprises reacting an allene compound of formula (1)

(1)

wherein $R_1$, $R_2$, $R_3$ and $R_4$ may be the same or different and each represents hydrogen, $C_{1-4}$ alkyl or $(R_5)_3Si$—, or $R_1$ and $R_2$, together with the carbon atom bonding them, may form 3- to 6-member ring, or $R_2$ and $R_3$, together with the allene bond group bonding them, may form 8- to 10-member ring, $R_5$s may be the same or different and independently of one another represent linear or branched $C_{1-4}$ alkyl, with an enol compound of formula (3)

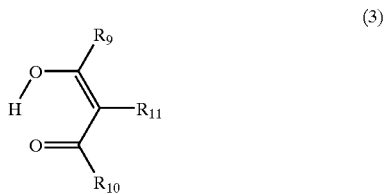

(3)

wherein $R_9$ and $R_{10}$ may be the same or different and each represents linear or branched $C_{1-4}$ alkyl, $C_{1-4}$ alkoxy, or linear or branched $C_{1-4}$ fluoroalkyl, $R_{11}$ represents hydrogen or fluorine in the presence of a copper(I) compound.

Next, the process for producing a β-diketonatocopper(I) complex according to the present invention will be explained in more detail on the basis of reaction formulae (A) and (B).

REACTION FORMULA (A)

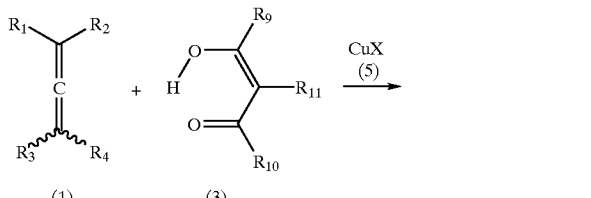

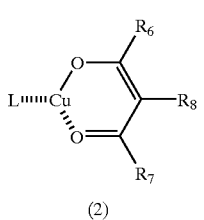

(2)

REACTION FORMULA (B)

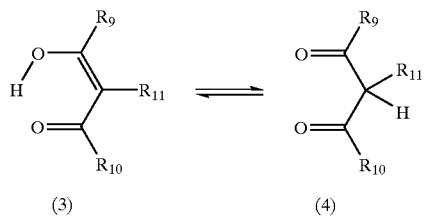

in formula (1) in reaction formula (A), $R_1$, $R_2$, $R_3$ and $R_4$ may be the same or different and each represents hydrogen, $C_{1-4}$ alkyl or $(R_5)_3Si$—, or $R_1$ and $R_2$, together with the carbon atom bonding them, may form 3- to 6-member ring, or $R_2$ and $R_3$, together with the allene bond group bonding them, may form 8- to 10-member ring, $R_5$s may be the same or different and independently of one another represent linear or branched $C_{1-4}$ alkyl, in formula (3) or (4), $R_9$ and $R_{10}$ may be the same or different and each represents linear or branched $C_{1-4}$ alkyl, $C_{1-4}$ alkoxy, or linear or branched $C_{1-4}$ fluoroalkyl, $R_{11}$ represents hydrogen or fluorine, in formula (2), $R_6$ and $R_7$ may be the same or different and each represents linear or branched $C_{1-4}$ alkyl, $C_{1-4}$ alkoxy, or linear or branched $C_{1-4}$ fluoroalkyl, $R_8$ represents hydrogen or fluorine, and L represents the allene compound of formula (1).

In the reaction represented by reaction formula (A), a β-diketonatocopper(I) complex in which an allene compound is coordinated can be synthesized by reacting an allene compound of formula (1) with an enol compound of formula (3) or a carbonyl compound of formula (4) (the compound of formula (4) is a tautomer of the compound of formula (3)) together with a copper(I) compound (CuX) of formula (5) optionally in the presence of a base (for example, inorganic base, such as sodium hydride, potassium hydride, sodium amide, potassium tertiary butoxide, potassium carbonate or the like).

The copper(I) compound includes, for example, $Cu_2O$, CuF, CuCl, CuBr, CuI, CuOAc, CuCN, CuSCN, CuOTf and so on.

The enol compound of formula (3) is a tautomer of the carbonyl compound of formula (4) as indicated in reaction formula (B).

The molar ratio of the allene compound to the enol compound may be arbitrarily set. However, it is preferable that the enol compound and allene compound are mixed in an amount equimolar or close thereto. For example, the molar ratio of the enol compound to the allene compound may be 0.5 to 1.5.

The molar ratio of the allene compound to the copper(I) compound may be arbitrarily set. However, it is preferable that copper atoms in the copper(I) compound are equimolar with allene compound or that an excessive of the copper atoms is mixed with the allene compound. For example, the molar ratio of the copper atoms to the allene compound may be 0.5 to 3. The molar ratio of the base to the allene compound may be arbitrarily set. However, it is preferable that the base is equimolar with the allene compound or that an excessive of the base is mixed with the allene compound. For example, the molar ratio of the base to the allene compound may be 0.5 to 3.

Although the reaction temperature is not particularly limited, the reaction may be carried out generally at a temperature between −110° C. and a boiling point of the solvent used in the reaction.

It is preferable to use solvents that do not participate in the reaction. The solvents that can be used include hydrocarbons (such as, hexane, pentane, benzene, toluene or the like), ethers (such as, diethyl ether, monoglyme, isopropyl ether, tetrahydrofuran, 1,4-dioxane or the like) and halogenated hydrocarbons (such as, dichloromethane, chloroform, dichloroethane or the like).

The β-diketonatocopper(I) complex according to the present invention is useful as a compound for forming a thin copper film by MOCVD method.

BEST MODE FOR CARRYING OUT THE INVENTION

The present invention will be concretely described on the basis of the following examples, but the present invention is not limited thereto at all.

EXAMPLE 1

Under nitrogen atmosphere, into 3.0 g of copper(I) oxide was poured 30 ml of dry dichloromethane that was fully degassed and the atmosphere of which was replaced with nitrogen to give a suspension solution. 1.77 g of 1-methyl-1-(trimethylsilyl) allene was added to the solution with vigorously stirring, then 3.2 g of 1,1,1,5,5,5-hexafluoro-2,4-pentanedione was slowly added from a dropping funnel. After the reaction solution was stirred for 12 hours, the solution was filtered under nitrogen atmosphere, and the filtrate was concentrated under reduced pressure at room temperature to give a green liquid. The liquid was purified through a column chromatography to give 4.2 g of [1-methyl-1-(trimethylsilyl) allene] (1,1,1,5,5,5-hexafluoro-2,4-pentanedionato) copper(I) containing 1-methyl-1-(trimethylsilyl) allene as a ligand represented by formula (6)

(6)

Me$_3$Si     Me
      \\   /
       C
       ‖
       C
      / \\
     H   H as an yellow liquid.

The resulting β-diketonatocopper(I) complex was identified with $^1$H-NMR and $^{13}$C-NMR.

$^1$H-NMR (δ, CDCl$_3$) 0.19 (s, 9H), 1.97–1.99 (m, 3H), 4.14–4.16 (m, 2H), 6.15 (s, 1H). $^{13}$C-NMR (δ, CDCl$_3$)–2.29 (3C), 17.09, 51.00, 90.21, 96.13, 117.69 (q, J$_{C-F}$=283.7 Hz, 2C), 173.87, 178.33 (q, J$_{C-C-F}$=34.5 Hz, 2C).

For evaluating the vaporization characteristic of the resulting β-diketonatocopper(I) complex, the thermogravimetric curve (heating rate: 10° C./min., under nitrogen atmosphere) was measured. Consequently, it was found that the complex has extremely high volatility and good vaporization characteristic. Boiling point: 140–164° C.

EXAMPLE 2

Under nitrogen atmosphere, into 3.0 g of copper(I) oxide was poured 30 ml of dry dichloromethane that was fully degassed and the atmosphere of which was replaced with nitrogen to give a suspension solution. 1.72 g of 1,2-cyclononadiene was added to the solution with vigorously stirring, then 3.23 g of 1,1,1,5,5,5-hexafluoro-2,4-pentanedione was slowly added from a dropping funnel. After the reaction solution was stirred for 4 hours, the solution was filtered under nitrogen atmosphere, and the filtrate was concentrated under reduced pressure at room temperature to give a green liquid.

The liquid was purified through a column chromatography to give 5.63 g of (1,2-cyclononadiene) (1,1,1,5,5,5-hexafluoro-2,4-pentanedionato) copper(I) containing 1,2-cyclononadiene as a ligand represented by formula (7)

(7)

as an yellow solid.

The resulting β-diketonatocopper(I) complex was identified with $^1$H-NMR and $^{13}$C-NMR.

$^1$H-NMR (δ, CDCl$_3$) 1.38–1.77 (m, 8H), 2.06–2.24 (m, 4H), 5.26–5.32 (m, 2H), 6.10 (s, 1H). $^{13}$C-NMR (δ, CDCl$_3$) 23.65, 25.49, 28.44, 88.28, 90.61, 118.65 (q, J$_{C-F}$=284.1 Hz, 2C), 173.83, 178.63 (q, J$_{C-C-F}$=34.6 Hz, 2C).

For evaluating the vaporization characteristic of the resulting β-diketonatocopper(I) complex, the thermogravimetric curve (heating rate: 10° C./min., under nitrogen atmosphere) was measured. Consequently, the complex had a melting point of 46.8° C. and a boiling point of 195.6° C.

EXAMPLE 3

In a similar manner as Example 2, starting from 3.0 g of copper(I) oxide, 1.30 g of 1,2-heptadiene and 3.23 g of 1,1,1,5,5,5-hexafluoro-2,4-pentanedione, 2.82 g of (1,2-heptadiene) (1,1,1,5,5,5-hexafluoro-2,4-pentanedionato) copper(I) containing 1,2-heptadiene as a ligand represented by formula (8)

(8)

n-Bu
  \\
   ‖
   C
   ‖ was obtained as an yellow liquid.

$^1$H-NMR (δ, CDCl$_3$) 0.89 (t, J=7.3 Hz, 3H), 1.30–1.42 (m, 2H), 1.42–154 (m, 2H), 2.15–2.27 (m, 2H), 4.33–4.40 (m, 2H), 5.45–5.55 (m, 1H), 6.13 (s, 1H). $^{13}$C-NMR (δ, CDCl$_3$) 13.95, 22.46, 31.50, 31.70, 55.72, 90.76, 92.44, 117.96 (q, J$_{C-F}$=283.7 Hz, 2C), 165.80, 178.85 (q, J$_{C-C-F}$=34.5 Hz, 2C).

For evaluating the vaporization characteristic of the resulting β-diketonatocopper(I) complex, the thermogravimetric curve (heating rate: 10° C./min., under nitrogen atmosphere) was measured. Consequently, the complex had a boiling point of 150.0° C.

EXAMPLE 4

In a similar manner as Example 2, starting from 3.0 g of copper(I) oxide, 2.16 g of 1-(dimethyl-tert-butylsilyl) allene and 3.23 g of 1,1,1,5,5,5-hexafluoro-2,4-pentanedione, 3.47 g of [(1-(dimethyl-tert-butylsilyl) allene)] (1,1,1,5,5,5-hexafluoro-2,4-pentanedionato) copper(I) containing 1-(dimethyl-tert-butylsilyl) allene as a ligand represented by formula (9)

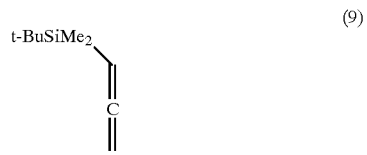

was obtained as an yellow liquid.

$^1$H-NMR (δ, CDCl$_3$) 0.20 (s, 6H), 0.97 (s, 9H), 4.35 (d, J=4.0 Hz, 2H), 4.87 (t, J=4.4 Hz, 1H), 6.15 (s, 1H). $^{13}$C-NMR (δ, CDCl$_3$) −5.40, 18.72, 26.61, 55.36, 69.50, 90.93, 117.94 (q, J$_{C-F}$=283.8 Hz, 2C), 159.51, 178.96 (q, J$_{C-C-F}$=34.8 Hz, 2C).

For evaluating the vaporization characteristic of the resulting β-diketonatocopper(I) complex, the thermogravimetric curve (heating rate: 10° C./min., under nitrogen atmosphere) was measured. Consequently, the complex had a boiling point of 140.0° C.

EXAMPLE 5

In a similar manner as Example 2, starting from 3.0 g of copper(I) oxide, 1.54 g of 1-(tert-butyl)-2-methyl allene and 3.23 g of 1,1,1,5,5,5-hexafluoro-2,4-pentanedione, 1.78 g of [1-(tert-butyl)-2-methyl allene] (1,1,1,5,5,5-hexafluoro-2,4-pentanedionato) copper(I) containing 1-(tert-butyl)-2-methyl allene as a ligand represented by formula (10)

was obtained as an yellow liquid.

$^1$H-NMR (δ, CDCl$_3$) 1.18 (s, 9H), 1.89–1.98 (m, 3H), 5.30–5.40 (m, 2H), 6.11 (s, 1H). $^{13}$C-NMR (δ, CDCl$_3$) 18.42, 30.41, 36.41, 79.79, 90.77, 93.20, 117.94 (q, J$_{C-F}$=283.8 Hz, 2C), 150.16, 178.78 (q, J$_{C-C-F}$=34.9 Hz, 2C).

For evaluating the vaporization characteristic of the resulting β-diketonatocopper(I) complex, the thermogravimetric curve (heating rate: 10° C./min., under nitrogen atmosphere) was measured. Consequently, the complex had a boiling point of 147.0° C.

EXAMPLE 6

Under nitrogen atmosphere, into 3.0 g of copper(I) oxide was poured 30 ml of dry dichloromethane that was fully degassed and the atmosphere of which was replaced with nitrogen to give a suspension solution. 0.96 g of 1,1-dimethyl allene was added to the solution with vigorously stirring, then 3.2 g of 1,1,1,5,5,5-hexafluoro-2,4-pentanedione was slowly added from a dropping funnel. After the reaction solution was stirred for 12 hours, the solution was filtered under nitrogen atmosphere, and the filtrate was concentrated under reduced pressure at room temperature to give a green liquid.

The liquid was purified through a column chromatography to give 2.3 g of (1,1-dimethyl allene) (1,1,1,5,5,5-hexafluoro-2,4-pentanedionato) copper(I) containing 1,1-dimethyl allene as a ligand represented by formula (11)

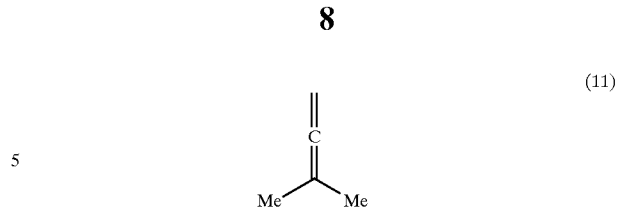

as an yellow liquid.

The resulting β-diketonatocopper(I) complex was identified with $^1$H-NMR and $^{13}$C-NMR.

$^1$H-NMR (δ, CDCl$_3$) 1.96 (t, J=2.8 Hz, 6H), 4.16 (t, J=2.8 Hz, 2H), 6.16 (s, 1H). $^{13}$C-NMR (δ, CDCl$_3$) 22.63 (2C), 50.03, 90.24, 108.41, 117.75 (q, J$_{C-F}$=284.9 Hz, 2C), 175.10, 178.40 (q, J$_{C-C-F}$=34.7 Hz, 2C).

EXAMPLE 7

Under nitrogen atmosphere, into 3.0 g of copper(I) oxide was poured 30 ml of dry dichloromethane that was fully degassed and the atmosphere of which was replaced with nitrogen to give a suspension solution. 1.35 g of 1,1,3,3-tetramethyl allene was added to the solution with vigorously stirring, then 3.2 g of 1,1,1,5,5,5-hexafluoro-2,4-pentanedione was slowly added from a dropping funnel. After the reaction solution was stirred for 12 hours, the solution was filtered under nitrogen atmosphere, and the filtrate was concentrated under reduced pressure at room temperature to give a green liquid.

The liquid was purified through a column chromatography to give 3.8 g of (1,1,3,3-tetramethyl allene) (1,1,1,5,5,5-hexafluoro-2,4-pentanedionato) copper(I) containing 1,1,3,3-tetramethyl allene as a ligand represented by formula (12)

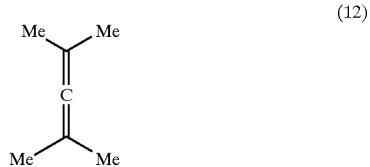

as an yellow solid.

The resulting β-diketonatocopper(I) complex was identified with $^1$H-NMR and $^{13}$C-NMR.

$^1$H-NMR (δ, CDCl$_3$) 2.00 (s, 12H), 6.18 (s, 2H). $^{13}$C-NMR (δ, CDCl$_3$) 24.84 (4C), 90.50 (2C), 93.25 (2C), 117.81 (q, J$_{C-F}$=285.3 Hz, 4C), 145.33, 178.61 (q, J$_{C-C-F}$=34.7 Hz, 4C).

Table 1 indicates the β-diketonatocopper(I) complexes (including ones synthesized in Examples described above) of the present invention synthesized according to the producing process or Examples described above along with allene compounds of their ligands (L) [formula (1)], but the present invention is not limited thereto.

TABLE 1

(1)

[Structure showing R1, R2, R3, R4 around C=C with wavy bond]

[Eight copper complex structures with L----Cu bound to various β-diketonate ligands:
- CF3/H/CF3
- CF3/H/Me
- CF3/H/Bu-t
- C3F7/H/Bu-t
- Bu-t/H/Bu-t
- Me/H/Me
- CF3/H/OMe with Me substituent
- Me/H/OBu-t]

| R₁ | R₂ | R₃ | R₄ |
|---|---|---|---|
| H | H | H | H |
| H | Me | H | H |
| H | Et | H | H |
| H | n-Pr | H | H |
| H | n-Bu | H | H |
| H | i-Pr | H | H |
| H | i-Bu | H | H |
| H | s-Bu | H | H |
| H | t-Bu | H | H |
| H | Me₃Si | H | H |
| H | Et₃Si | H | H |
| H | n-Pr₃Si | H | H |
| H | n-Bu₃Si | H | H |
| H | i-Pr₃Si | H | H |
| H | Me₂(Et)Si | H | H |
| H | Me₂(n-Pr)Si | H | H |
| H | Me₂(i-Pr)Si | H | H |
| H | Me₂(t-Bu)Si | H | H |
| Me | Me | H | H |
| Me | Et | H | H |
| Me | n-Pr | H | H |
| Me | n-Bu | H | H |
| Me | i-Pr | H | H |
| Me | i-Bu | H | H |
| Me | s-Bu | H | H |
| Me | t-Bu | H | H |
| Me | Me₃Si | H | H |
| Me | Et₃Si | H | H |
| Me | n-Pr₃Si | H | H |
| Me | n-Bu₃Si | H | H |
| Me | i-Pr₃Si | H | H |

TABLE 1-continued

| R₁ | R₂ | R₃ | R₄ |
|---|---|---|---|
| Me | Me₂(Et)Si | H | H |
| Me | Me₂(n-Pr)Si | H | H |
| Me | Me₂(i-Pr)Si | H | H |
| Me | Me₂(t-Bu)Si | H | H |
| Et | Et | H | H |
| Et | n-Pr | H | H |
| Et | n-Bu | H | H |
| Et | i-Pr | H | H |
| Et | i-Bu | H | H |
| Et | s-Bu | H | H |
| Et | t-Bu | H | H |
| n-Pr | n-Pr | H | H |
| n-Pr | n-Bu | H | H |
| n-Pr | i-Pr | H | H |
| n-Pr | i-Bu | H | H |
| n-Pr | s-Bu | H | H |
| n-Pr | t-Bu | H | H |
| n-Bu | n-Pr | H | H |
| n-Bu | i-Pr | H | H |
| n-Bu | i-Bu | H | H |
| n-Bu | s-Bu | H | H |
| n-Bu | t-Bu | H | H |
| Me₃Si | Et | H | H |
| Me₃Si | n-Pr | H | H |
| Me₃Si | n-Bu | H | H |
| Me₃Si | i-Pr | H | H |
| Me₃Si | i-Bu | H | H |
| Me₃Si | s-Bu | H | H |
| Me₃Si | t-Bu | H | H |
| n-Bu₃Si | Et | H | H |
| n-Bu₃Si | n-Pr | H | H |
| n-Bu₃Si | n-Bu | H | H |
| n-Bu₃Si | i-Pr | H | H |
| n-Bu₃Si | i-Bu | H | H |
| n-Bu₃Si | s-Bu | H | H |
| n-Bu₃Si | t-Bu | H | H |
| Me₂(t-Bu)Si | Et | H | H |
| Me₂(t-Bu)Si | n-Pr | H | H |
| Me₂(t-Bu)Si | n-Bu | H | H |
| Me₂(t-Bu)Si | i-Pr | H | H |
| Me₂(t-Bu)Si | i-Bu | H | H |
| Me₂(t-Bu)Si | s-Bu | H | H |
| Me₂(t-Bu)Si | t-Bu | H | H |
| Me₃Si | Me₃Si | H | H |
| Me₃Si | Me₂(t-Bu)Si | H | H |
| —(CH₂)₂— | | H | H |
| —(CH₂)₅— | | H | H |
| Me | H | Me | H |
| Me | H | Et | H |
| Me | H | n-Pr | H |
| Me | H | n-Bu | H |
| Me | H | i-Pr | H |
| Me | H | i-Bu | H |
| Me | H | s-Bu | H |
| Me | H | t-Bu | H |
| Me | H | Me₃Si | H |
| Me | H | Et₃Si | H |
| Me | H | n-Pr₃Si | H |
| Me | H | n-Bu₃Si | H |
| Me | H | i-Pr₃Si | H |
| Me | H | Me₂(Et)Si | H |
| Me | H | Me₂(n-Pr)Si | H |
| Me | H | Me₂(i-Pr)Si | H |
| Me | H | Me₂(t-Bu)Si | H |
| Et | H | Et | H |
| Et | H | n-Pr | H |
| Et | H | n-Bu | H |
| Et | H | i-Pr | H |
| Et | H | i-Bu | H |
| Et | H | s-Bu | H |
| Et | H | t-Bu | H |
| n-Pr | H | n-Pr | H |
| n-Pr | H | n-Bu | H |
| n-Pr | H | i-Pr | H |
| n-Pr | H | i-Bu | H |
| n-Pr | H | s-Bu | H |
| n-Pr | H | t-Bu | H |
| n-Bu | H | n-Pr | H |
| n-Bu | H | i-Pr | H |

TABLE 1-continued

| | | | |
|---|---|---|---|
| n-Bu | H | i-Bu | H |
| n-Bu | H | s-Bu | H |
| n-Bu | H | t-Bu | H |
| Me₃Si | H | Et | H |
| Me₃Si | H | n-Pr | H |
| Me₃Si | H | n-Bu | H |
| Me₃Si | H | i-Pr | H |
| Me₃Si | H | i-Bu | H |
| Me₃Si | H | s-Bu | H |
| Me₃Si | H | t-Bu | H |
| n-Bu₃Si | H | Et | H |
| n-Bu₃Si | H | n-Pr | H |
| n-Bu₃Si | H | n-Bu | H |
| n-Bu₃Si | H | i-Pr | H |
| n-Bu₃Si | H | i-Bu | H |
| n-Bu₃Si | H | s-Bu | H |
| n-Bu₃Si | H | t-Bu | H |
| Me₂(t-Bu)Si | H | Et | H |
| Me₂(t-Bu)Si | H | n-Pr | H |
| Me₂(t-Bu)Si | H | n-Bu | H |
| Me₂(t-Bu)Si | H | i-Pr | H |
| Me₂(t-Bu)Si | H | i-Bu | H |
| Me₂(t-Bu)Si | H | s-Bu | H |
| Me₂(t-Bu)Si | H | t-Bu | H |
| Me₃Si | H | Me₃Si | H |
| Me₃Si | H | Me₂(t-Bu)Si | H |
| H | —(CH₂)₆— | | H |
| H | —(CH₂)₇— | | H |
| Me | Me | Me | H |
| Me | Et | Me | H |
| Me | Et | i-Bu | H |
| Me | i-Bu | Me | H |
| Me | Me | Me₃Si | H |
| Me | Me₃Si | n-Bu | H |
| n-Bu | Me₃Si | Me | H |
| Me | Me₃Si | Me₃Si | H |
| Me₃Si | Me₃Si | Me₃Si | H |
| —(CH₂)₄— | | Me | H |
| —(CH₂)₅— | | Me | H |
| Me | —(CH₂)₆— | | H |
| Me | Me | Me | Me |
| Me | n-Bu | Me | Me |
| Me | Me₃Si | Me | n-Pr |
| n-Bu | Me₃Si | Me | Me |
| Me | Me₃Si | n-Bu | n-Bu |
| Me₃Si | Me₃Si | Me₃Si | Me₃Si |
| —(CH₂)₅— | | Me | n-Pr |

Industrial Applicability

The present invention provides novel β-diketonatocopper (I) complexes and processes for producing the same. The β-diketonatocopper(I) complexes according to the present invention are useful as compounds for forming a thin copper film by MOCVD method.

What is claimed is:

1. A β-diketonatocopper(I) complex which contains as a ligand (L) an allene compound of formula (1)

(1)

wherein $R_1$, $R_2$, $R_3$ and $R_4$ may be the same or different and each represents hydrogen, $C_{1-4}$ alkyl or $(R_5)_3Si$—, or $R_1$ and $R_2$, together with the carbon atom bonding them, may form 3- to 6-member ring, or $R_2$ and $R_3$, together with the allene bond group bonding them, may form 8- to 10-member ring, $R_5$s may be the same or different and independently of one another represent linear or branched $C_{1-4}$ alkyl, and which is represented by formula (2)

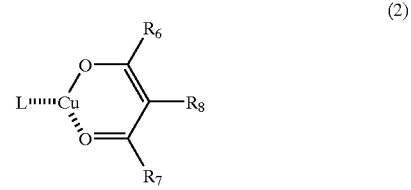

(2)

wherein, $R_6$ and $R_7$ may be the same or different and each represents linear or branched $C_{1-4}$ alkyl, $C_{1-4}$ alkoxy, or linear or branched $C_{1-4}$ fluoroalkyl, $R_8$ represents hydrogen or fluorine, and L represents the allene compound of formula (1).

2. A process for producing a β-diketonatocopper(I) complex represented by formula (2)

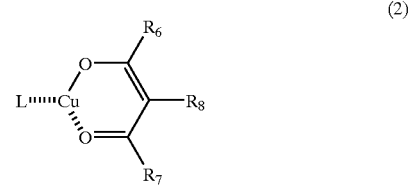

(2)

wherein, $R_6$ and $R_7$ may be the same or different and each represents linear or branched $C_{1-4}$ alkyl, $C_{1-4}$ alkoxy, or linear or branched $C_{1-4}$ fluoroalkyl, $R_8$ represents hydrogen or fluorine, and L represents the allene compound of formula (1), characterized in that the process comprises reacting an allene compound of formula (1)

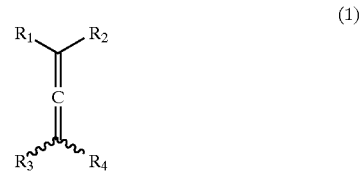

(1)

wherein $R_1$, $R_2$, $R_3$ and $R_4$ may be the same or different and each represents hydrogen, $C_{1-4}$ alkyl or $(R_5)_3Si$—, or $R_1$ and $R_2$, together with the carbon atom bonding them, may form 3- to 6-member ring, or $R_2$ and $R_3$, together with the allene bond group bonding them, may form 8- to 10-member ring, $R_5$s may be the same or different and independently of one another represent linear or branched $C_{1-4}$ alkyl, with an enol compound of formula (3)

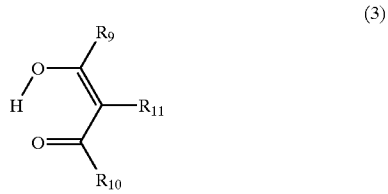

(3)

wherein $R_9$ and $R_{10}$ may be the same or different and each represents linear or branched $C_{1-4}$ alkyl, $C_{1-4}$ alkoxy, or linear or branched $C_{1-4}$ fluoroalkyl, $R_{11}$ represents hydrogen or fluorine in the presence of a copper(I) compound.

* * * * *